United States Patent
Lemmens et al.

(10) Patent No.: US 9,750,447 B2
(45) Date of Patent: Sep. 5, 2017

(54) LIGHTING SYSTEM WITH MONITORING FUNCTION

(71) Applicant: KONINKLIJKE PHILIPS N.V., Eindhoven (NL)

(72) Inventors: Paul Marcel Carl Lemmens, Veghel (NL); Murray Fulton Gillies, Eindhoven (NL); Juergen Vogt, Kamen (DE)

(73) Assignee: Koninklijke Philips N.V., Eindhoven (NL)

( * ) Notice: Subject to any disclaimer, the term of this patent is extended or adjusted under 35 U.S.C. 154(b) by 184 days.

(21) Appl. No.: 14/354,731

(22) PCT Filed: Oct. 17, 2012

(86) PCT No.: PCT/IB2012/055662
§ 371 (c)(1),
(2) Date: Apr. 28, 2014

(87) PCT Pub. No.: WO2013/061215
PCT Pub. Date: May 2, 2013

(65) Prior Publication Data
US 2014/0288382 A1   Sep. 25, 2014

Related U.S. Application Data

(60) Provisional application No. 61/552,520, filed on Oct. 28, 2011.

(51) Int. Cl.
*A61B 5/16* (2006.01)
*A61B 5/11* (2006.01)
(Continued)

(52) U.S. Cl.
CPC .............. *A61B 5/16* (2013.01); *A61B 5/0077* (2013.01); *A61B 5/1124* (2013.01);
(Continued)

(58) Field of Classification Search
CPC ... A61B 5/0059; A61B 5/0077; A61B 5/1124; A61B 5/1128; A61B 5/16; A61B 5/165;
(Continued)

(56) References Cited

U.S. PATENT DOCUMENTS 7,324,076 B2   1/2008   Lee
8,977,371 B2   3/2015   Ashdown
(Continued)

FOREIGN PATENT DOCUMENTS

CN   201491337 U   5/2010
CN   102000378 A   4/2011
(Continued)

*Primary Examiner* — Amanda Patton

(57) ABSTRACT

In summary the invention utilizes a patient's interaction with a user interface 120 of a controllable lighting system 100. The user interface enables light characteristics of the lighting system 100 to be adjusted such as the light color emitted from a light source 110 of the lighting system 100. A monitor 130 is provided for monitoring how the patient interacts with the user interface 120, e.g. by monitoring how frequent the patient interacts with the user interface, the monitored number of interactions may be processed by a processor 140 to determine a value of the coping style which indicates how active or passive the patient is.

13 Claims, 1 Drawing Sheet

(51) Int. Cl.
*A61M 21/00* (2006.01)
*A61B 5/00* (2006.01)
*A61M 21/02* (2006.01)

(52) U.S. Cl.
CPC ............ *A61B 5/1128* (2013.01); *A61B 5/165* (2013.01); *A61B 5/4884* (2013.01); *A61B 5/7475* (2013.01); *A61M 21/00* (2013.01); *A61B 5/0059* (2013.01); *A61B 5/746* (2013.01); *A61M 21/02* (2013.01); *A61M 2021/0044* (2013.01); *A61M 2205/332* (2013.01); *A61M 2205/505* (2013.01); *A61M 2230/63* (2013.01)

(58) Field of Classification Search
CPC ..... A61B 5/4884; A61B 5/746; A61B 5/7475; A61M 2021/0044; A61M 21/00; A61M 21/02; A61M 2205/332; A61M 2205/505
See application file for complete search history.

(56) References Cited

U.S. PATENT DOCUMENTS

| 2005/0122712 | A1* | 6/2005 | Kim ................... F21V 5/008 362/184 |
|---|---|---|---|
| 2005/0163302 | A1 | 7/2005 | Mock et al. |
| 2009/0009341 | A1 | 1/2009 | Gak |
| 2010/0023094 | A1 | 1/2010 | Smith et al. |
| 2011/0207100 | A1 | 8/2011 | Brokken et al. |
| 2014/0288382 | A1 | 9/2014 | Lemmens et al. |

FOREIGN PATENT DOCUMENTS

| KR | 20060036068 A | 4/2006 |
|---|---|---|
| WO | 2008084208 A2 | 7/2008 |
| WO | 2010029918 A1 | 3/2010 |
| WO | 2010046834 A2 | 4/2010 |
| WO | 2011146969 A1 | 12/2011 |

\* cited by examiner

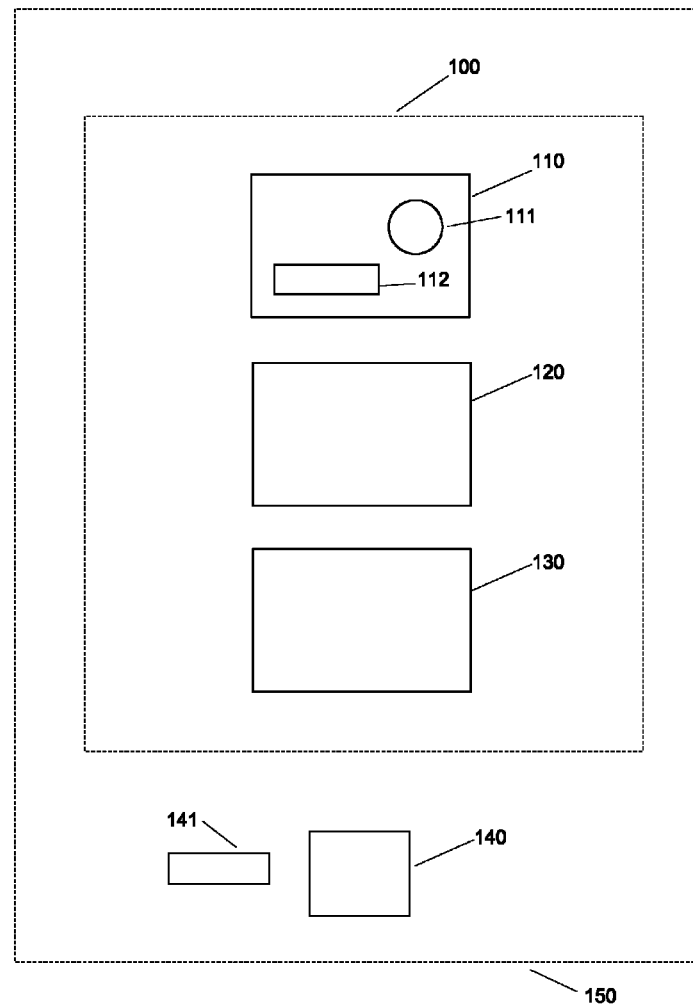

LIGHTING SYSTEM WITH MONITORING FUNCTION

This application is a national stage application under 35 U.S.C. §371 of International Application No. PCT/IB2012/055662 filed on Oct. 17, 2012 and published in the English language on May 2, 2013 as International Publication No. WO/2013/061215, which claims priority to U.S. Application No. 61/552,520 filed on Oct. 28, 2011, the entire disclosures of which are incorporated herein by reference.

FIELD OF THE INVENTION

The invention relates to monitoring of patient's behavior, particularly to monitoring patient's behavior for determining a level of active and passive behavior.

BACKGROUND OF THE INVENTION

For many people that experience psychological problems there is a clear link to the lack of perceived control over their environment and events in their life. The feeling of lack of control is often caused or increased by stressful situations. How an individual responds to this stress is often referred to as the coping style.

Coping style may be accessed via a questionnaire. One of the more important axes to assess in the coping style is whether someone is passive or active, i.e. if someone—when put under stress—will try to interact more with their environment or will withdraw and become less interactive in an effort to relax and de-escalate.

It is well known that the coping style is reflected in the patient's interaction with his environment. Patients with an active coping style have the tendency to move around a lot, fidget or interact with objects without a specific purpose.

Knowing the coping style of a patient is important within the treatment of mental problems as the caregiver's method of interacting with the patient may be adjusted if the personality trait is known.

Accordingly, there is a need to determine the coping style of a patient and, therefore, the inventor of the present invention has devised the present invention.

SUMMARY OF THE INVENTION

It would be advantageous to achieve improvements within determination of patient conditions, such as a patient's level of active or passive behavior, i.e. a patient's coping style. It would be desirable to enable a device to determine such patient condition automatically without involving other persons than the patient. In particular, it may be seen as an object of the present invention to provide a method that addresses the above mentioned needs, or solves related problems of the prior art.

To better address one or more of these concerns, in a first aspect of the invention a lighting system is presented comprising:

a light source which is controllable to generate different light characteristics, a user interface with selectable light characteristics for selection of a light characteristic of the light source, and a monitor for monitoring interaction of the user with the user interface.

By monitoring the user's interaction with the user interface the obtained information can be used to characterize the patient's coping style. A user's interaction with the user interface may comprise selections of light characteristics, for example how often a new light color, such as a hue, is selected. For example, frequent selections of light colors may indicate a patient with an active coping style. Such information may be used by the caregiver to give the optimal treatment to the patient. Another type of monitored interactions with the user interface may comprise measurement of key-pressure, i.e. how hard buttons of the user interface are pressed.

As an example, the light source could be a LED lamp such as the Philips Living Colours LED lamp. The light source may be combined with a separate monitor, and possibly a separate user interface. Some control device may be required for enabling data communication between the user interface and the light source or between the user interface and the monitor.

In an embodiment the lighting system may comprise an output for communicating the monitored interaction of the user with the user interface to a processing unit for determining a patient condition from the monitored selections of the user interface.

The output may enable wired or wireless communication of monitored data representing the monitored selections to a separate external processing unit, e.g. a stand-alone computer, and/or the output may enable communication of monitored data to an internal processing unit included with the lighting system. A display may be included in the lighting system to display a determined patient condition.

In an embodiment the light characteristics may comprise light color characteristics. Accordingly, different hues or light wavelengths may be selected from the user interface. Other selectable light color characteristics than hue comprise saturation and brightness characteristics of the emitted light. The user interface may provide buttons or other selector for selecting the light color characteristics. The selector may be in the form of discrete color buttons or in the form of color diagrams such as a color wheel displaying a substantially continuously changing color from which a light color can be selected.

Herein, light color characteristics is defined as comprising hue, saturation and brightness, and color is understood as a specific combination of hue, saturation and brightness parameters. Accordingly, the user may be able to select specific parameters of hue, saturation and/or brightness or the user may be able to select a color which is composed of a specific combination of hue, saturation and brightness. Thus, when reference is made to color herein, this is understood as comprising any of the parameters hue, saturation or brightness or a combination thereof.

In an embodiment the monitor may be configured for monitoring one or more of the following parameters: a period of time where a user selects light characteristics from the user interface, a duration of a key press, a pressure exerted on a button for selecting a light characteristic, a number of selections of light characteristics of the user interface, a finally selected light characteristic, a similarity of presently selected light characteristics with previously selected light characteristics, and motion of the user interface.

A long period of time of interaction with the user interface may indicate that the patient has an active coping style since the patient interacts a lot with the user interface. Similarly, a high number of selections may indicate an active coping style. A finally selected light color may indicate an active or passive coping style, e.g. selection of a red color may indicate an active coping style. Selection of light characteristics which most often is similar to previously selected light characteristics may indicate a patient with a passive coping style.

In an embodiment the user interface is configured for adapting what characteristics are selectable. For example, the user interface may be configured to enable selection of light characteristics using the patient's previous interaction with the user interface so that in a given situation (e.g. a high stress situation) the patient is only presented with light characteristics which the patient found pleasant in an earlier situation (e.g. in situations where the patient showed mental improvements). The user interface may also be configured for adapting according to the more recent selections of light characteristics. For example, if the last ten selections show that the patient has a need for selecting other light colors, the adaptable user interface may be expanded to provide other selectable light characteristics. The user interface may also be configured for adapting in response to a specific coping style of the patient; e.g., a level of active or passive behavior may be entered as an input to the lighting system via the user interface or other input so as to adapt the user interface to that patient characteristic. Thus, the user interface may be automatically adapted in response to monitored quantities of the user's interaction with the user interface, or the user interface may be manually adapted in response to input (e.g. input indicating a coping style) to the lighting system provided by a care giver, the patient or other personnel.

In an embodiment the monitor comprises a camera for monitoring the interaction of the user with the user interface. A camera for monitoring said interaction may be beneficial when selectable selectors are projected onto a wall by a light beamer. Furthermore, a camera may monitor the selected light characteristics by monitoring the light outputted from the light source 110 and, thereby, direct monitoring of the user interface may be unnecessary.

In an embodiment the user interface may be moveable and the motion of the user interface may be monitored for determining an activity level of the user. According to this embodiment, the monitor may also be configured to monitor motion data of the user interface.

As second aspect of the invention relates to a patient monitoring system comprising:
the lighting system according to the first aspect,
a processing unit for determining a patient condition from the monitored selections of the user interface by use of a patient prediction function.

In one embodiment the processing unit of the patient monitoring system is configured to adapt the patient prediction function dependent upon a mismatch between a patient condition determined by the processing unit and a known patient condition. By employing self-learning capabilities the automatic prediction of patient conditions may be improved further.

The processing unit may alternatively or additionally be configured to determine the patient condition from monitored motion of the user interface.

A third aspect of the invention relates to a method for determining a patient condition where the method comprises:
monitoring user selections on a user interface, where the user interface provides selectable light characteristics which can be generated by light source,
processing the monitored user selections so as to determine the patient condition.

The patient condition, e.g. coping style, is understood as the trait of the patient which at a given moment in time is being expressed in the state of the person.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the FIG. 1 which shows a lighting system 100 and a patient monitoring system 140.

DESCRIPTION OF EMBODIMENTS

In summary the invention utilizes a patient's interaction with a user interface of a controllable lighting system. The user interface enables light characteristics of the lighting system to be adjusted such as the light color emitted from the lighting system. By monitoring how the patient interacts with the user interface, e.g. by monitoring how frequent the patient interacts with the user interface, the monitored number of interactions may be used to determine a value of the coping style which indicates how active or passive the patient is.

FIG. 1 shows a lighting system 100 which includes a light source 110 which is controllable to generate different light characteristics such as different light colors and light intensities. The light source may include a light emission device 111, e.g. a LED panel capable of emitting light of different colors, and a light controller 112 for controlling the LED panel dependent upon an input signal.

The light source 110 or the entire lighting system 100 may be in the form of a stand-alone lamp, e.g. a Philips LED light, a ceiling light or other light. The light source is primarily intended for room lighting capable of generating an individualized light environment for single rooms such as comfort rooms, isolation rooms or other patient rooms. The individualized light environment generally has a positive effect on the patient in crisis and ideally helps with achieving a rapid de-escalation back to a normal stress level. For optimum de-escalation the patient should have control of the setting of the light characteristics of the light source 110.

The lighting system 100 also comprises a user interface 120 with selectable light characteristics for selection of a light characteristic of the light source. The user interface may be in the form of remote control with buttons for selecting light characteristics, a control panel integrated with the light source 110 or a touch sensitive screen such as a touch sensitive screen of a smart phone. In an embodiment the user interface 120 may be a light beamer capable of projecting virtual buttons onto a wall, where the patient's selection of a button may be detected by a camera.

The controller 112 may have an input for receiving signals from the user interface 120 and for converting the input signal to a driving signal to the light emitting device 111.

The lighting system 100 also comprises a monitor for monitoring the patient's interaction with the user interface, e.g. for monitoring the patient's selections of the user interface. Thus, the monitor may be configured to monitor a period of time where a user selects light characteristics from the user interface, a duration of a key press, a number of selections of light characteristics of the user interface, e.g. within a fixed time period or before a final characteristic is chosen, motion of the user interface (particularly relevant when the user interface is moveable), or a finally selected light characteristic. The monitor may also be configured to determine the similarity of presently selected light characteristics with previously selected light characteristics to determine the consistency of the patient's selections.

In an embodiment the user interface is provided with pressure sensors for measuring how hard the user presses a given button when the user uses that button for selecting a light characteristic. Advantageously, monitoring of a patient's interaction with the user interface may comprise monitoring of key-pressures.

The monitoring may be performed visually by a camera capable of viewing buttons projected by a light beamer onto a wall or capable of viewing and determining the actual light characteristic emitted by the light emission device 111. Alternatively, the monitoring may be performed by monitoring optical or electrical signals from the user interface or signals outputted by the light controller 112.

A processing unit 140 may be provided for determining a patient condition from the monitored selections of the user interface. Thus, the processing unit may convert the patient's interaction with the user interface as being monitored by the monitor 130 into a patient condition or value of the coping style by use of a patient condition function 141, e.g. an algorithm, a prediction model or some look up table. For example, an average frequency of selections (over a given period) may be directly converted to a number indicating the activity level of the patient.

The processing unit 140 may be able to adapt the algorithm, look up table or some model used for determining the patient condition depending upon a mismatch between a patient condition determined by the processing unit 140 and a known patient condition, i.e., a patient condition determined by qualified clinical personnel. Accordingly, a patient monitoring system 150 comprising the processing unit 140 may have a self-learning function embodied by a capability which enables the patient prediction function (e.g. a look up table) to be adapted in response to a mismatch between the predicted patient condition and a true patient condition.

In general the patient condition may comprise a stress value, a value indicating whether the patient is active or passive, or a value of the coping style. A determined patient condition may generate an alarm if a threshold is exceeded.

The processing unit 140 may be an external unit which receives real time monitored selections or stored selections from the lighting system 100, e.g. from the monitor 130. For example, a processing unit 140 in the form of a computer may be wire or wirelessly connected to the lighting system for receiving monitored selections and for processing the monitored selections.

Alternatively, the processing unit may be integrated with the lighting system 100 and configured so that only authorized persons are able to inspect the determined patient condition.

Whether the processing unit 140 is a separate unit or integrated with the lighting system 100, the combination of the processing unit 140 and the lighting system 100 is referred to as a patient monitoring system 150.

The processing unit may be configured to process computer program code to perform functions of predicting patient conditions or adapting the patient prediction function in response to mismatches between predicted and true patient conditions.

The light source 110, the user interface 120 and the monitor 130 may be separate devices capable of communicating data between devices or they may be integrated into one or more devices.

The user interface may be configured for adapting what light characteristics are selectable in response to an input control signal, such as an input signal representing the currently or recently selected light characteristics (e.g. on basis of the last ten selections), an input signal representing a usage history based on stored selections (e.g. on basis of selections from a previous day or week), or an input signal generated or provided by a care giver or other person. In this way the light characteristics which are selectable by the patient may be adapted to suit the patient's need, e.g. a few selectable light characteristics may be made selectable in order not to stress a patient or to suit a passive patient, or a larger number of light characteristics may be made selectable to suit a more active patient.

The adaptable user interface may be realized by a light beamer or a touch screen which can be controlled to display selectable buttons of varying size, number or appearance.

The user interface such as a remote controller or touch screen may be moveable by the patient or carried by the patient. Such a moveable user interface may include a position detector, e.g., an accelerometer, capable of detecting the movement of the user interface and, thereby, the movement of the patient. Thus, in an embodiment the motion of the user interface is monitored for determining an activity level of the user. Accordingly, the processing unit 140 may be configured to determine a patient condition from the monitored motion of the of the user interface. Thus, a high level of movement of the user interface could indicate an active coping style and a low level of movement could indicate a passive coping style.

In an embodiment where the user interface is embodied by a light beamer, the light beamer may advantageously also be used for displaying video. A video may be selectable by the user from a library of videos. The library may be adapted depending upon the monitored selections of light characteristics or the library may be adapted by a caregiver or other person to adapt the selectable videos to the patient's mental situation or coping style. There may also be a physical interaction intentionally induced by the video and the patient's motive reaction measured by the motion of the user interface and in turn used to assess coping style.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:
1. A lighting system, comprising:
a light source that is directly controllable by a user to generate selected light characteristics from a plurality of selectable light characteristics,
a user interface that enables the user to directly control the light source to concurrently produce a desired set of light characteristics, and
a monitor that monitors interactions of a user with the user interface, wherein the user interface is configured to modify the light characteristics that are selectable by the user, based on previous interactions of the user with the user interface, and where the lighting system comprises an output for communicating the monitored interaction of the user with the user interface to a processing unit that determines a condition of the user from the monitored interaction of the user with the user interface.

2. The lighting system of claim 1, wherein the selectable light characteristics include light color characteristics.

3. The lighting system of claim 1, wherein the monitor is configured to monitor one or more of the following parameters: a period of time when a user selects the desired light characteristics from the user interface, a duration of a key press, a pressure exerted on a button for selecting the desired light characteristic, a number of selections of light characteristics of the user interface, a finally selected desired light characteristic, a similarity of presently selected desired light characteristics with previously selected desired light characteristics, and motion of the user interface.

4. The lighting system of claim 1, wherein the monitor comprises a camera that monitors interaction of the user with the user interface.

5. The lighting system of claim 1, where the light source is a LED lamp.

6. A patient monitoring system comprising:
the lighting system of claim 1,
a processing unit that includes a patient prediction function that determines a condition of a patient based on the patient's interaction with the user interface.

7. The patient monitoring system of claim 6, wherein the processing unit modifies the patient prediction function based on a comparison of the patient condition determined by the processing unit and a known patient condition.

8. A method for determining a patient condition, comprising:

providing a user interface that enables a patient to directly control a light source to concurrently provide a select set of characteristics of the light source from a plurality of characteristics that are selectable by the patient, monitoring selections of the patient on the user interface that produce a desired set of characteristics of the light source, processing the monitored selections so as to determine the patient condition, and modifying the characteristics that are selectable by the patient, based on previous interactions of the patient with the user interface.

9. The method of claim 8, where the characteristics that are selectable by the patient includes light color characteristics.

10. The method of claim 8, wherein the processing of the monitored selections is performed at a processing unit that is external to the light source, and the method includes communicating the monitored selections to the processing unit.

11. The method of claim 8, wherein the monitoring of the selections is performed at a processing unit that is external to the light source.

12. The method of claim 8, wherein the monitoring of the selections includes monitoring camera images of the user with the user interface.

13. The method of claim 8, wherein the monitoring of the selections includes monitoring one or more of the following parameters: a period of time when the patient selects the desired set of characteristics from the user interface; a duration of a key press; a pressure exerted on a button for selecting a characteristic of the desired set of characteristics; a number of selections of characteristics of the light source; a finally selected desired characteristic; a similarity of presently selected desired characteristics with previously selected desired characteristics; and motion of the user interface.

* * * * *